United States Patent [19]

Hosaka et al.

[11] 4,033,750

[45] July 5, 1977

[54] HERBICIDAL COMPOSITION

[75] Inventors: Hideo Hosaka; Hiromi Yoneda, both of Oiso, Japan

[73] Assignee: Nippon Soda Company Limited, Tokyo, Japan

[22] Filed: Sept. 4, 1975

[21] Appl. No.: 610,113

[30] Foreign Application Priority Data

Jan. 16, 1975 Japan .................. 50-6426
Sept. 14, 1974 Japan ............. 49-106538

[52] U.S. Cl. ........................ 71/90; 71/88
[51] Int. Cl.² .......................... A01N 9/22
[58] Field of Search .................. 71/90, 88

[56] References Cited

UNITED STATES PATENTS

| | | | |
|---|---|---|---|
| 2,756,135 | 7/1956 | Searle .................... | 71/90 |
| 3,198,786 | 8/1965 | Tilles et al. .............. | 71/88 X |
| 3,714,177 | 1/1973 | Engelhart ............... | 71/90 X |
| 3,818,024 | 6/1974 | Krenzer ................. | 71/90 X |
| 3,845,069 | 10/1974 | Schafer et al. ........... | 71/90 X |

Primary Examiner—Lewis Gotts
Assistant Examiner—Catherine L. Mills
Attorney, Agent, or Firm—George B. Oujevolk

[57] ABSTRACT

Mixture of a compound of the formula

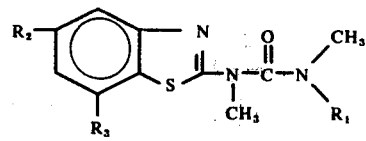

wherein
 $R_1$ and $R_3$ are hydrogen or methyl group,
 $R_2$ is lower alkyl group;
and S-ethyl hexahydro-1H-azepine-1-carbothioate have greater herbicidal activity.

2 Claims, No Drawings

HERBICIDAL COMPOSITION

DETAILED DESCRIPTION OF THE INVENTION:

This invention relates to new herbicidal compositions having enhanced effectiveness and to an improved method of killing weeds. The invention consists in providing mixtures of herbicidal compounds which are more effective than the individual components. More particularly, this invention is directed to compositions containing, as active herbicidal ingredient, the mixture of at least one compound selected from the group consisting of the compound of the following formula:

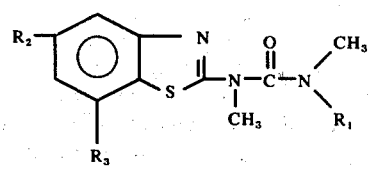

wherein
$R_1$ and $R_3$ are hydrogen or methyl group,
$R_2$ is lower alkyl;
and S-ethyl hexahydro-1H-azepine-1-carbothioate having the following formula:

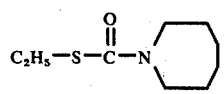

Especially preferred for use of its herbicidal effectiveness is the mixture of 1,3-dimethyl-3-(5-t-butylbenzothiazole-2yl)urea or 1,1,3-trimethyl-3-(5-ethylbenzothiazole-2-yl)urea and S-ethyl hexahydro-1H-azepine-1-carbothioate.

The herbicidal composition is chosen with view of the crop plant and the problem weed in that area. Frequently, the mixing of herbicides required to control certain combinations of weeds present produces a composition not only toxic to the objectionable weeds but also to the crop plants.

The purpose of the present invention is to provide mixtures of herbicides which have complementary effects and will therefore control a broader number of weed but do so at lower levels of application.

In one aspect, the present invention is a novel composition comprising two kinds of selective herbicides for broadleaf weeds and for watergrass.

It is a further object to provide an improved and more efficacious method for killing weeds.

The compounds of formula [I] can be prepared in accordance with the following equations:

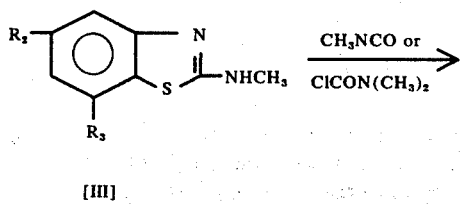

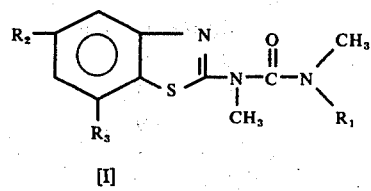

wherein $R_1$, $R_2$ and $R_3$ are as previously defined.

Some typical compounds of formula [I] which can be employed in combination in the composition of this invention are listed in Table 1.

Table 1

| Compound No. | $R_1$ | $R_2$ | $R_3$ | Physical Constant |
|---|---|---|---|---|
| 1 | H | $CH_3$ | H | m.p. 139 – 140° C |
| 2 | $CH_3$ | $CH_3$ | H | m.p. 72 – 74° C |
| 3 | $CH_3$ | $C_2H_5$ | H | $n_D^{20}$ 1.6061 |
| 4 | H | $C_4H_9^t$ | H | m.p. 109 – 110° C |
| 5 | H | $CH_3$ | $CH_3$ | m.p. 131 – 132° C |
| 6 | $CH_3$ | $CH_3$ | $CH_3$ | m.p. 95 – 96° C |
| 7 | H | $C_2H_5$ | H | m.p. 94 – 96° C |
| 8 | H | $C_3H_7^i$ | H | m.p. 99 – 101° C |
| 9 | H | $C_3H_7^n$ | H | $n_D^{20}$ 1.5913 |
| 10 | H | $C_4H_9^n$ | H | $n_D^{21}$ 1.5962 |

Hereinafter, the compound of the formula [I] are represented by compound No. in Table 1.

As mentioned previously, it has been found that the mixture of a compound of formula [I] and S-ethyl hexahydro-1H-azipine-1-carbothioate has a synergetic herbicidal activity in addition to a cumulatively increased activity of those each selective herbicidal functions.

The compound of above formula [I] is particularly effective in the control of broad leaf weeds and Cyperus weeds.

It has been disclosed in U.S. Pat. No. 3,198,786 that S-ethyl hexahydro-1H-azepine-1-carbothioate has herbicidal properties and is used for controlling grass weeds, especially barnyard grass. But it is less effective against broad leaf weeds and Cyperus weeds when it is applied in paddy field, and this is one drawback for the above-mentioned herbicidal compound.

However, by means of blending a compound of formula [I] with above-mentioned S-ethylhexahydro-1H-azepine-1-carbothioate, the mixed herbicidal composition is able to kill completely the objective weeds in smaller amount of application rate compared with the individual components and further, phytotoxicity against crops can be remarkable mitigated.

In the practice of this invention the compound of the formula [I] may be mixed with 1/10–20 times, preferably ½–5 times of S-ethyl hexahydro-1H-azepine-1-carbothioate, that is to say, mixtures of from 5 to 95% by weight of each component may be used, but with 30 to 70% of each optimum results are obtained, and the resulting mixture exhibits a strong herbicidal effect and thereby a perfect weed control can be expected.

The mixed composition of this invention can be applied directly to the soil as preemergence treatment or to plant foliage, as post-emergence treatment, or they can be mixed intimately with the soil and may be applied to soil or plant foliar at rates of over 50 g of active ingredients per 10 are, preferably over 100 g per 10 are.

The method of the present invention comprehends the employment of a liquid or solid composition containing two or more of the compounds of formula [I]

and S-ethyl hexahydro-1H-azepine-1-carbothioate as an active ingredient.

The active ingredient of this invention may be formulated by mixing with suitable carriers in a form generally used in agricultural chemicals such as wettable powder, emulsifiable concentrate, dust formulation, granulare formulation, water soluble powder and aerosol. As solid carriers, bentonite, diatomaceous earth, apatite, gypsum, talc, pyrophyllite, vermiculite, clay and others are used. As liquid carriers, water, kerosene, mineral oil, petroleum, solvent naphtha, benzene, xylene, cyclohexane, cyclohexanone, dimethylformamide, alcohol, acetone, and others are used. Sometimes surface active agent is added in order to give a homogeneous and stable formulation.

The composition of this invention also can be applied admixed with other chemicals which are used in agronomic and horticultural management. Such chemicals can be, but are not restricted to, the classes of chemicals commonly known as plant nutrients, fertilizers, insecticides, acaricides, fungicides, herbicides and nematocides.

The concentrations of the active ingredients in the herbicidal composition of this invention vary according to type of formulation, and they are, for example, used in a range of 5–80 weight percent, preferably 10–60 weight percent, in wettable powder, 5–70 weight percent, preferably 20–60 weight percent, in emulsifiable concentrates, and 0.5–30 weight percent, preferably 1–10 weight percent in dust formulation.

Thus, a wettable powder or an emulsifiable concentrate produced thereto is diluted with water to a specified concentration and thereby, it is used as a liquid suspension or a liquid emulsion for treating soils or plant foliars. Further, a dust formulation is directly used for the soil treatment or the foliar treatment.

The non-limiting examples for the herbicidal composition of the present invention are illustrated as follows:

Example 1.

| Emulsifiable Concentrate | Parts by weight |
| --- | --- |
| Compound 1 | 20 |
| S-ethyl hexahydro-1H-azepine-1-carbothioate | 20 |
| Xylene | 35 |
| Dimethylformamide | 15 |
| Polyoxyethylene phenylether | 10 |

These are mixed and dissolved.

Consequently, emulsifiable concentrate containing 40% of the active ingredient is obtained. In practical use, it is diluted to a certain concentration with water and then is sprayed as an emulsion.

Example 2.

| Wettable Powder | Parts by weight |
| --- | --- |
| Compound 2 | 10 |
| S-ethyl hexahydro-1H-azepine-1-carbothioate | 30 |
| Diatomaceous earth | 23 |
| Sodium alkylsulfate | 8 |
| Talc | 29 |

These are mixed homogeneously and reduced to fine particles. Consequently, wettable powder containing 40% of active ingredient is obtained. In practical use, it is diluted to a certain concentration with water and is sprayed as a suspension.

Example 3.

| Granular Formulation | Parts by weight |
| --- | --- |
| Compound 3 | 2 |
| S-ethyl hexahydro-1H-azepine-carbothioate | 5 |
| Talc | 35 |
| Clay | 35 |
| Bentonite | 16 |
| Sodium alkylsulfate | 7 |

These are mixed homogeneously and reduced to fine particles. Fine particles are made into granules having the diameter in the range of 0.5–1.0 mm by granulator.

Consequently, granular formulations containing 7% of the active ingredient are obtained. In practical use they are directly applied.

Example 4.

| Emulsifiable Concentrate | Parts by weight |
| --- | --- |
| Compound 4 | 25 |
| S-ethyl hexahydro-1H-azepine-1-bothioate | 15 |
| Xylene | 35 |
| Dimethylformamide | 15 |
| Polyoxyethylene phenylether | 10 |

These are mixed and dissolved.

Consequently, emulsifiable concentrate containing 40% of the active ingredient is obtained. In practical use, it is diluted to certain concentration with water and then is sprayed as emulsion.

The following tests were carried out to compare the herbicidal effectiveness of the mixed composition of the present invention with that of single active ingredient.

Test 1. Field test

Seeds of barnyard grass (*Echinochloa crus-galli*) were planted in a paddy field and rice plants (variety: Nihonbare) were transplanted in that field. Eighteen days after transplantation, the granular formulations containing test comounds were sprayed on the surface of the soil.

The stages of rice plant and weeds at the time of spraying are as follows:
- rice plant: 2nd tillering stage
- barnyard grass: 1st–4th leaf-stage
- umbrella plant: 2nd–4th leaf-stage
- monochoria: 2nd–3rd leaf-stage
- other broad leaf weeds: germination — development of first leaf Thirty days after spraying, the degrees of damage to the plants were observed and estimated by the valves of 0 — which have the following meanings:
- 0: no effect
- 1: partial plant slightly injured
- 2: plant slightly injured
- 3: plant moderately injured
- 4: plant severely injured
- 5: plant completely killed or no germination The results are shown in Table 2.

Table 2

| Compound No. | Application rate of test compound (g/10 ares) S-ethyl hexahydro-1H-azepine-1-carbothioate | barnyard grass | umbrella plant | monochoria | other broad leaf weeds | rice plant |
|---|---|---|---|---|---|---|
| 3 | 135 | 0 | 0 | 3 | 5 | 5 | 0 |
|   | 180 | 0 | 0 | 4 | 5 | 5 | 0 |
|   | 240 | 0 | 0 | 4 | 5 | 5 | 0 |
|   | 0 | 180 | 3 | 0 | 0 | 0 | 0 |
|   | 0 | 240 | 4 | 0 | 0 | 0 | 0 |
|   | 45 | 180 | 5 | 5 | 5 | 5 | 0 |
|   | 90 | 180 | 5 | 5 | 5 | 5 | 0 |
|   | 135 | 180 | 5 | 5 | 5 | 5 | 0 |
|   | 180 | 180 | 5 | 5 | 5 | 5 | 0 |
|   | 240 | 180 | 5 | 5 | 5 | 5 | 0 |
|   | 45 | 240 | 5 | 5 | 5 | 5 | 0 |
|   | 90 | 240 | 5 | 5 | 5 | 5 | 0 |
|   | 135 | 240 | 5 | 5 | 5 | 5 | 0 |
|   | 180 | 240 | 5 | 5 | 5 | 5 | 0 |
|   | 240 | 240 | 5 | 5 | 5 | 5 | 0 |
| Simetryne 45 | 180 | 3 | 4 | 5 | 5 | 0 |
| Simetryne 45 | saturn 210 | 3 | 5 | 5 | 5 | 0 |
| 4 | 90 | 0 | 0 | 3 | 2 | 4 | 0 |
|   | 135 | 0 | 0 | 4 | 3 | 5 | 0 |
|   | 180 | 0 | 2 | 5 | 4 | 5 | 0 |
|   | 240 | 0 | 3 | 5 | 5 | 5 | 1 |
|   | 0 | 180 | 4 | 0 | 1 | 0 | 0 |
|   | 0 | 240 | 5 | 1 | 2 | 2 | 0 |
|   | 45 | 180 | 4 | 5 | 4 | 5 | 0 |
|   | 90 | 180 | 5 | 5 | 5 | 5 | 0 |
|   | 135 | 180 | 5 | 5 | 5 | 5 | 0 |
|   | 180 | 180 | 5 | 5 | 5 | 5 | 0 |
|   | 240 | 180 | 5 | 5 | 5 | 5 | 1 |
|   | 45 | 240 | 5 | 5 | 5 | 5 | 0 |
|   | 90 | 240 | 5 | 5 | 5 | 5 | 0 |
|   | 135 | 240 | 5 | 5 | 5 | 5 | 0 |
|   | 180 | 240 | 5 | 5 | 5 | 5 | 0 |
|   | 240 | 240 | 5 | 5 | 5 | 5 | 1 |
| Simetryne 45 | 180 | 4 | 4 | 5 | 5 | 0 |
| Simetryne 45 | saturn 210 | 4 | 5 | 5 | 5 | 0 |
| 5 | 45 | 0 | 0 | 3 | 5 | 5 | 0 |
|   | 90 | 0 | 0 | 3 | 5 | 5 | 0 |
|   | 180 | 0 | 0 | 4 | 5 | 5 | 0 |
| 6 | 45 | 0 | 0 | 3 | 5 | 5 | 0 |
|   | 90 | 0 | 1 | 4 | 5 | 5 | 0 |
|   | 180 | 0 | 1 | 4 | 5 | 5 | 2 |
|   | 0 | 180 | 3 | 0 | 0 | 0 | 0 |
|   | 0 | 225 | 5 | 0 | 0 | 0 | 0 |
|   | 0 | 270 | 5 | 1 | 0 | 0 | 0 |
| 5 | 45 | 180 | 5 | 5 | 5 | 5 | 0 |
|   | 90 | 180 | 5 | 5 | 5 | 5 | 0 |
| 6 | 90 | 180 | 5 | 5 | 5 | 5 | 0 |
| Simetryne 45 | 180 | 3 | 4 | 5 | 5 | 0 |
| Simetryne 45 | saturn 210 | 3 | 5 | 5 | 5 | 0 |
|   | Untreated | 0 | 0 | 0 | 0 | 0 |

Simetryne: 2,4-bis(ethylamino)-6-methylmercapto-s-triazine
Saturn: S-(4-chlorobenzyl)-N,N-diethylthiol carbamate Test 2.

After seeds of barnyard grass (*Echinochloa crusgalli*), monochoria (*Monochoria vaginalis*) and bulrush (*Scirpus juncoides*) were planted in a pot having 2,500 square centimeters and covered slightly with soil, a sedge (*Cyperus seropinus*) and spikerush (*Eleocharis acicularis*) were transplanted to said pot and further pre-soaked seeds of rice plant were planted or young rice-plants were transplanted.

Seven days after planting of seeds of rice plant or transplanting of young rice-plants, the granular formulations containing test compounds were sprayed on the surface of the soil. The stages of rice plant and weeds at the time of spraying are as follows:

rice plant: directly seeded — 1.5 leaf stage transplanted — first tillering stage
barnyard grass: germination — 3rd leaf stage
monochoria: germination — 1st leaf stage
bulrush: germination starting stage
sedge: germination starting stage Fourteen days after spraying, the degrees of damage to the plants were observed and estimated by the value of 0–5 which have the same meanings as those of Test 1. The results are shown in Table 3.

Table 3

| Compound No. | Application rate (g/10 are) | S-ethyl hexahydro-1H-azepine-1-carbothioate | barnyard grass | monochoria | bulrush | sedge | spikerush | other broad leaf weeds | rice plant transplanted | rice plant directly seeded |
|---|---|---|---|---|---|---|---|---|---|---|
| 3 | 45 | 0 | 1 | 5 | 1 | 5 | 2 | 5 | 0 | 0 |
|   | 90 | 0 | 1 | 5 | 3 | 5 | 2 | 5 | 0 | 0 |
|   | 180 | 0 | 3 | 5 | 4 | 5 | 3 | 5 | 0 | 0 |
|   | 360 | 0 | 5 | 5 | 5 | 5 | 4 | 5 | 0 | 0 |
|   | 0 | 180 | 3 | 0 | 0 | 0 | 1 | 0 | 0 | 0 |
|   | 0 | 240 | 5 | 0 | 0 | 0 | 2 | 0 | 0 | 0 |
|   | 45 | 180 | 5 | 5 | 5 | 5 | 5 | 5 | 0 | 0 |
|   | 90 | 180 | 5 | 5 | 5 | 5 | 5 | 5 | 0 | 0 |
|   | 135 | 180 | 5 | 5 | 5 | 5 | 5 | 5 | 0 | 0 |
|   | 180 | 180 | 5 | 5 | 5 | 5 | 5 | 5 | 0 | 0 |
|   | 90 | 240 | 5 | 5 | 5 | 5 | 5 | 5 | 0 | 0 |
|   | 135 | 240 | 5 | 5 | 5 | 5 | 5 | 5 | 0 | 0 |
|   | 180 | 240 | 5 | 5 | 5 | 5 | 5 | 5 | 0 | 0 |
|   | 240 | 240 | 5 | 5 | 5 | 5 | 5 | 5 | 0 | 0 |
| 5 | 45 | 0 | 1 | 5 | 1 | 3 | 2 | 5 | 0 | 0 |
|   | 90 | 0 | 1 | 5 | 2 | 5 | 2 | 5 | 0 | 0 |
|   | 180 | 0 | 2 | 5 | 4 | 5 | 3 | 5 | 0 | 0 |
| 6 | 45 | 0 | 1 | 5 | 1 | 3 | 2 | 5 | 0 | 0 |
|   | 90 | 0 | 2 | 5 | 1 | 4 | 3 | 5 | 0 | 1 |
|   | 180 | 0 | 3 | 5 | 4 | 4 | 3 | 5 | 0 | 2 |
|   | 0 | 180 | 5 | 0 | 1 | 0 | 3 | 0 | 0 | 0 |
|   | 0 | 225 | 5 | 0 | 2 | 0 | 4 | 0 | 0 | 0 |
|   | 0 | 270 | 5 | 1 | 3 | 0 | 4 | 0 | 0 | 0 |
| 5 | 45 | 180 | 5 | 5 | 5 | 5 | 5 | 5 | 0 | 0 |
|   | 90 | 180 | 5 | 5 | 5 | 5 | 5 | 5 | 0 | 0 |
| 6 | 45 | 180 | 5 | 5 | 5 | 5 | 5 | 5 | 0 | 0 |
|   | 90 | 180 | 5 | 5 | 5 | 5 | 5 | 5 | 0 | 0 |
| Simetryne 45 |  | 180 | 4 | 5 | 3 | 0 | 4 | 5 | 0 | 4 |
| Untreated |  |  | 0 | 0 | 0 | 0 | 0 | 0 | 0 | 0 |

It is to be observed therefore that the present invention provides for a herbicidal composition which is a benzothiazole derivative. The starting material is obtained by procedures described in standard reference works and indeed, a leading article on the subject will be found in Raymond E. Kirk et al, Encyclopedia of Chemical Technology, Interscience Encyclopedia, Inc., New York, Vol. 7, 1951 Edition, Article on Heterocyclic Compounds, pages 442, 443.

What is claimed is:

1. A herbicidal composition comprising an inert carrier, and a herbicidally effective amount of a mixture of 1,3-dimethyl-3-(5-t-butylbenzothiazole-2-yl) urea and S-ethyl hexahydro-1H-azepine-1-carbothioate in a urea-carbothioate ratio of 1:1 to 1:2 parts by weight.

2. A method for the control of weeds comprising applying a herbicidal composition of claim 1 in an amount sufficient to exert herbicidal action to a locus to be protected.

* * * * *